United States Patent
Huelskamp et al.

(10) Patent No.: US 9,320,883 B2
(45) Date of Patent: Apr. 26, 2016

(54) AUTO-CONFIGURATION CIRCUIT FOR SAFETY MODE OPERATION OF IMPLANTABLE MEDICAL DEVICE

(71) Applicant: Cardiac Pacemakers, Inc., St. Paul, MN (US)

(72) Inventors: Paul Huelskamp, St. Paul, MN (US); Douglas J. Gifford, Ham Lake, MN (US); Scott A. Reedstrom, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/547,728

(22) Filed: Nov. 19, 2014

(65) Prior Publication Data

US 2015/0151131 A1   Jun. 4, 2015

Related U.S. Application Data

(60) Provisional application No. 61/910,647, filed on Dec. 2, 2013.

(51) Int. Cl.

| | |
|---|---|
| A61N 1/08 | (2006.01) |
| A61N 1/02 | (2006.01) |
| G06F 19/00 | (2011.01) |
| A61N 1/37 | (2006.01) |
| A61N 1/36 | (2006.01) |
| A61N 1/372 | (2006.01) |
| A61N 1/362 | (2006.01) |
| G06F 9/44 | (2006.01) |
| G06F 9/445 | (2006.01) |

(52) U.S. Cl.
CPC *A61N 1/025* (2013.01); *A61N 1/37* (2013.01); *G06F 19/3412* (2013.01); *A61N 1/362* (2013.01); *A61N 1/3605* (2013.01); *A61N 1/36142* (2013.01); *A61N 1/3718* (2013.01); *A61N 1/37264* (2013.01); *G06F 9/4401* (2013.01); *G06F 9/44505* (2013.01)

(58) Field of Classification Search
None
See application file for complete search history.

(56) References Cited

U.S. PATENT DOCUMENTS

| | | | |
|---|---|---|---|
| 6,061,599 A | 5/2000 | Rhodehamel et al. | |
| 6,128,528 A * | 10/2000 | Ericksen | A61N 1/37 607/2 |
| 6,662,049 B1 * | 12/2003 | Miller | A61N 1/3931 607/27 |
| 7,363,080 B2 * | 4/2008 | Stubbs | A61N 1/362 607/27 |
| 7,937,151 B2 | 5/2011 | Maniak et al. | |
| 8,381,724 B2 | 2/2013 | Bowen et al. | |
| 2007/0091687 A1 * | 4/2007 | Armstrong | A61N 1/37264 365/185.29 |
| 2011/0160786 A1 * | 6/2011 | Stubbs | A61N 1/37 607/14 |

* cited by examiner

*Primary Examiner* — Kennedy Schaetzle
(74) *Attorney, Agent, or Firm* — Schwegman Lundberg & Woessner, P.A.

(57) ABSTRACT

An implantable medical device comprises a non-volatile memory circuit including a configuration memory portion to store auto-configuration data for the IMD, a controller circuit, a reset circuit adapted to generate a reset signal and disable the controller circuit, and a startup circuit adapted to transfer the auto-configuration data from the configuration memory portion to one or more configuration registers in response to the reset signal, wherein values of the one or more configuration registers configure the IMD for a safety mode operation.

20 Claims, 5 Drawing Sheets

AUTO-CONFIGURATION CIRCUIT FOR SAFETY MODE OPERATION OF IMPLANTABLE MEDICAL DEVICE

CLAIM OF PRIORITY

This application claims the benefit of priority under 35 §119(e) of U.S. Provisional Patent Application Ser. No. 61/910,647, filed on Dec. 2, 2011, which is herein incorporated by reference in its entirety.

BACKGROUND

Implantable medical devices (IMDs) can include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The sense amplifiers may be included in an electronics unit that performs diagnostic functions and functions related to delivery of therapy. IMDs can also include neural stimulation devices to provide electrical stimulation or other therapy to a portion of the nervous system of the patient. The electronics unit often includes microcontrollers or microprocessors along with memory to store information such as program instructions and data. The present inventors have recognized a need for improved reliability and improved design flexibility of IMDs.

OVERVIEW

This document relates generally to systems, devices, and methods for auto-configuration of an IMD. An apparatus example can be implantable and include a non-volatile memory circuit including a configuration memory portion to store auto-configuration data for the IMD, a controller circuit, a reset circuit adapted to generate a reset signal and disable the controller circuit, and a startup circuit adapted to transfer the auto-configuration data from the configuration memory portion to one or more configuration registers in response to the reset signal, wherein values of the one or more configuration registers configure the IMD for a safety mode operation.

This section is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An implantable medical device may include one or more of the features, structures, methods, or combinations thereof described herein. For example, an implantable cardiac monitor or cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
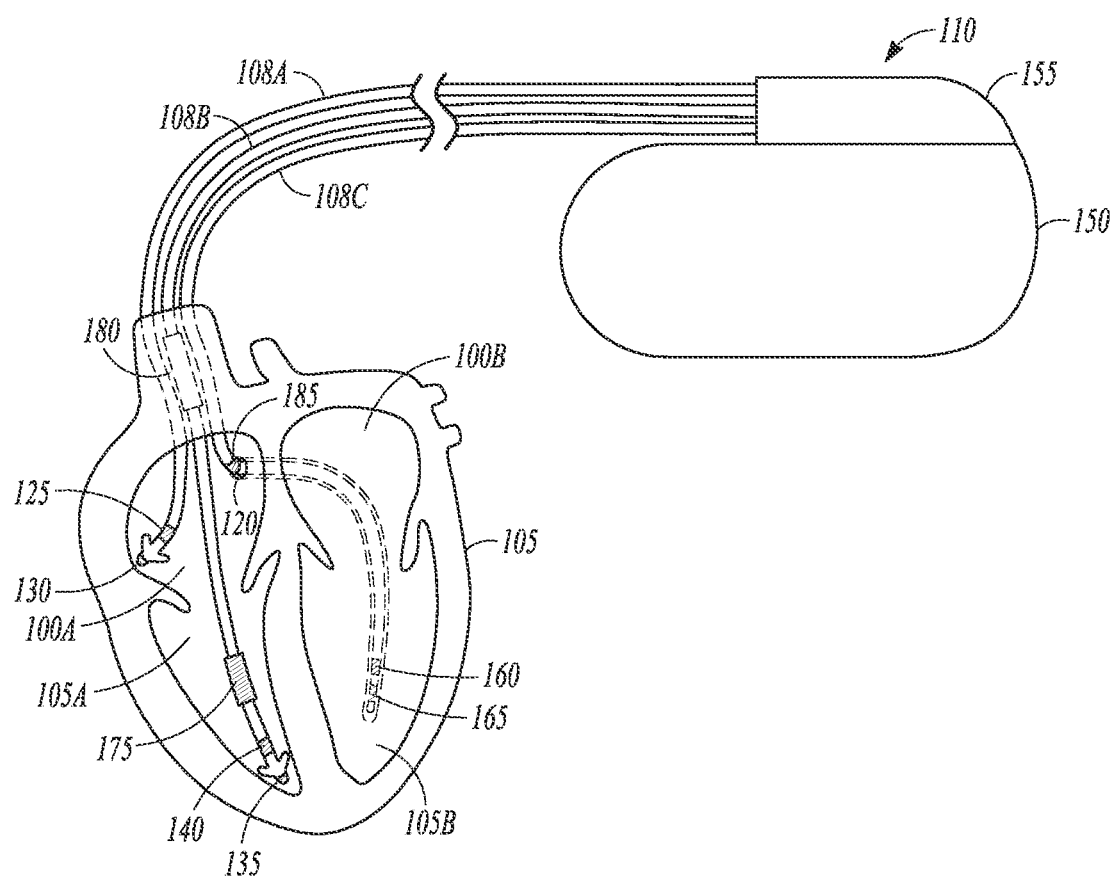
FIG. 1 illustrates portions of an example of an IMD.

This document discusses systems, devices and methods for improved default configuration of an implantable or partially implantable medical device. FIG. 1 illustrates portions of an example of an IMD 110. Examples of IMD 110 include, without limitation, a pacer, a defibrillator, a cardiac resynchronization therapy (CRT) device, or a combination of such devices. The IMD 110 is shown coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardio-version, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally provides resynchronization therapy to the heart 105. Resynchronization therapy is typically delivered to the ventricles in order to better synchronize the timing of depolarization between ventricles.

Lead 108B optionally also includes a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. In some examples, the coil electrodes 175, 180 are used in combination with other electrodes for sensing signals.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 120. Although only two electrodes are shown in the example of the Figure, lead 108C may include three electrodes, four electrodes, or any number of electrodes as desired.

Note that although a specific arrangement of leads and electrodes are shown in the illustration, the present methods and devices will work in a variety of configurations and with a variety of electrodes.

Figure 2:
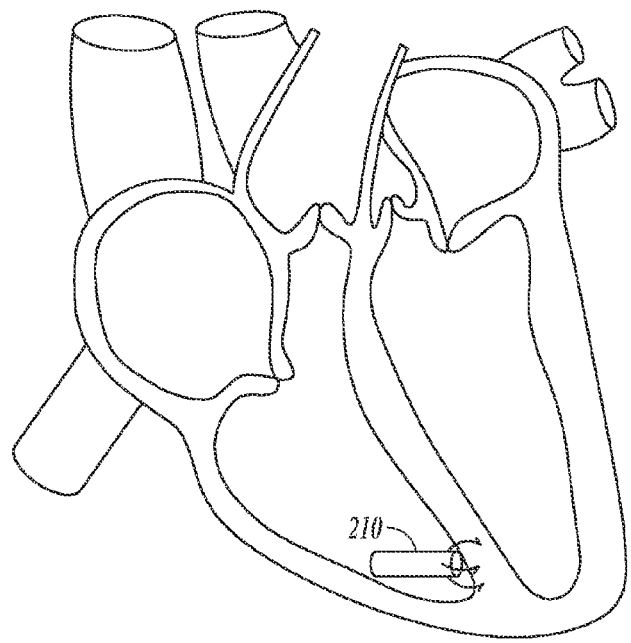
FIG. 2 illustrates portions of another example of an IMD.

FIG. 2 illustrates portions of another example of an IMD 210. The IMD 210 is leadless and is shown positioned at the endocardium within a ventricular chamber. The example of a leadless device shown in FIG. 2 has a rod or bullet shape and includes electrodes arranged along the cylindrical portion of the housing to provide electrical therapy to the heart.

Although the examples shown are designed to provide electrical cardiac therapy, other IMDs may provide different types of therapy. For instance, an IMD may include a neural stimulation device having electrodes configured by shape and size to deliver electrical therapy to a portion of the nervous system of the subject. In other examples, the IMD is a diagnostic device that only performs sensing and data gathering functions.

Generally, IMDs include an electronics unit to perform device functions, such as diagnostic functions and therapy functions for example. The electronics unit is typically included within a hermetically sealed housing and can include, among other things, one or more of sense amplifiers to sense electrical activity, signal processing circuits to interpret or detect events in a sensed signal, and timers to initiate and terminate functions performed by the device. IMDs can operate in a safety mode that can be initiated when an event occurs that indicates that the integrity of the device may be comprised, such as a memory fault or a failure of an electronic circuit for example. The safety mode may be a fallback mode that suspends activity of a significant portion of the electronics unit to avoid using circuits that may be compromised.

The electronics unit of an IMD can include one or more integrated circuits (ICs). The ICs may be designed to provide a safety mode and the operating features of the safety mode are determined at the time of the IC design. However, the operating features desired in the safety mode may change after the IC is designed. Also, the safety mode of an IMD that provides low energy therapy (e.g. a pacemaker) can be different from the safety mode of an IMD that provides high energy therapy (e.g. an ICD); yet a manufacturer may want to use one solid state platform for both the low energy device and the high energy device. These design challenges can be overcome by implementing an IMD to have a flexible automatic configuration.

Figure 3:
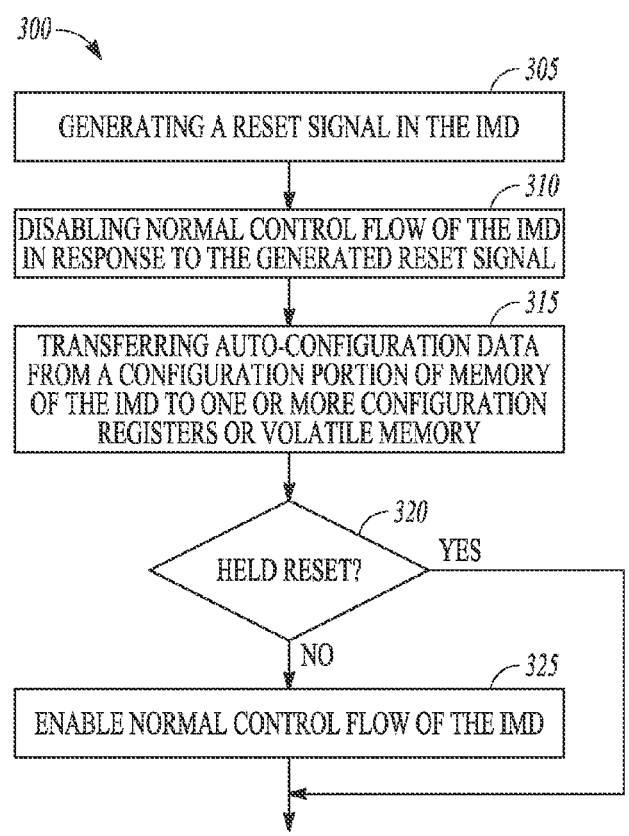
FIG. 3 shows a flow diagram of an example of a method of operating an IMD.

FIG. 3 shows a flow diagram of an example of a method 300 of operating an IMD to perform auto-configuration of the device. At block 305, a reset signal is generated in the IMD. The reset signal may be generated in response to a detected error or in response to the power supply rising to a specified voltage (e.g. a device startup).

At block 310, normal control flow of the IMD is disabled in response to the generated reset signal. This may involve disabling a portion of the electronics unit, such as by maintaining the portion in a reset state, or by disabling clock signals provided to the portion of the electronics unit.

At block 315, auto-configuration data is transferred from a configuration portion of non-volatile memory of the IMD to one or more configuration registers when the normal control flow of the IMD is disabled. In certain variations, the configuration registers can be a portion of non-volatile memory. Writing values into the configuration registers configures the IMD for the safety mode operation. Writing different values enables and disables different features. Thus, the auto-configuration can be made flexible by changing the auto-configuration data. Using non-volatile memory for the configuration data reduces the number of errors.

The auto-configuration data can be transferred from memory to the configuration registers or non-volatile memory by a mechanism separate from the normal control function of the IMD. For instance, the control mechanism may be a simple hardware state machine that operates only to transfer the data. In this way, the IMD may be configured to operate in safety mode without involving the normal operating circuits of the IMD, which may have been compromised to cause the device to enter the safety mode.

At block 320, if the portion of the electronics unit is not held in the reset state, flow continues to block 325 where normal control flow of the IMD is enabled.

Figure 4:
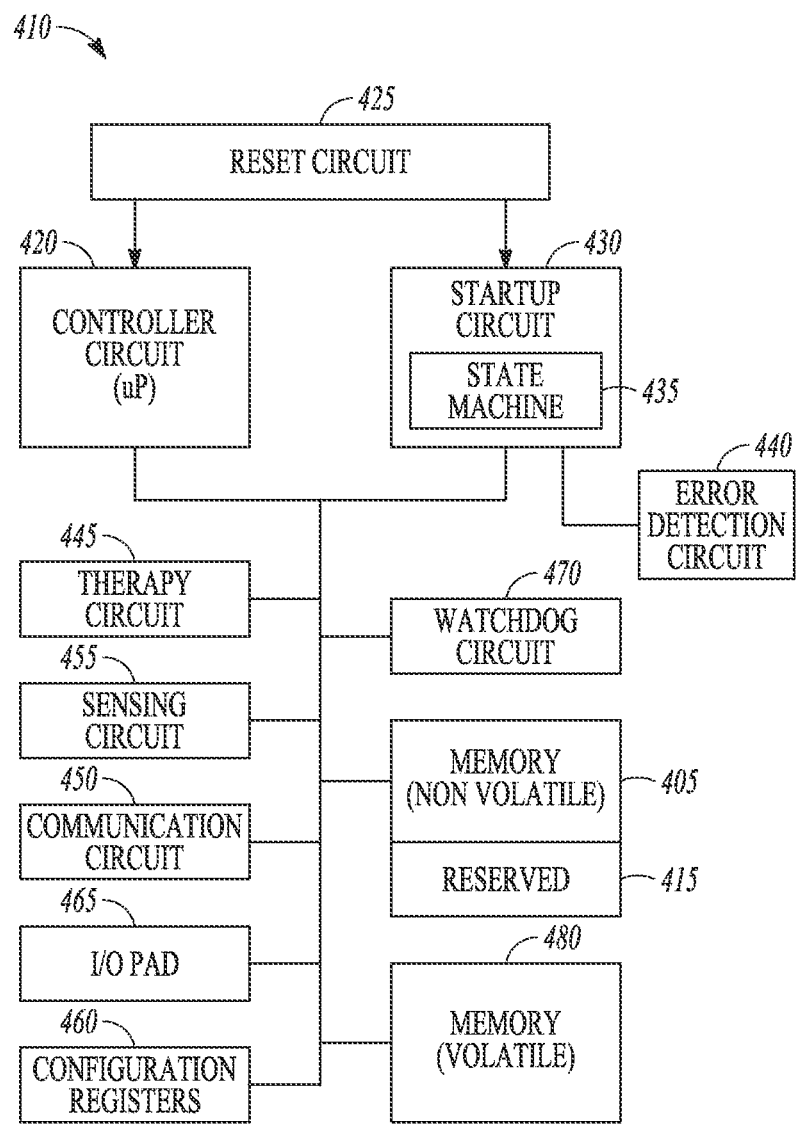
FIG. 4 shows a block diagram of portions of an example of an IMD with auto-configuration.

FIG. 4 shows a block diagram of portions of an example of an IMD 410 with auto-configuration. The IMD 410 includes a non-volatile memory circuit 405. The nonvolatile memory circuit includes a configuration memory portion 415 to store auto-configuration data for the IMD 410. The IMD 410 also includes a controller circuit 420. The controller circuit 420 performs or initiates the normal device functions in a normal mode of operation.

In some examples, the controller circuit 420 includes a processor (e.g., a microprocessor) that executes instructions (e.g. instructions included in firmware) to perform functions related to one or both of diagnostics and therapy. In some examples, the controller circuit 420 includes a finite state machine (FSM). A state machine progresses through a predefined set of device states according to triggering events or conditions. The device can enter the individual states according to a clock event (e.g., sequentially) or according to a triggering event or detected condition. The states of the device can be defined by memory, hardware circuits or a combination of memory and hardware. The device performs one or more of the functions described by progressing through the device states.

The IMD 410 also includes a reset circuit 425 and a startup circuit 430. The reset circuit 425 is adapted to generate a reset signal and disable the controller circuit, and the startup circuit 430 is adapted to transfer the auto-configuration data from the configuration memory portion to one or both of configuration registers 460 and non-volatile memory in response to the reset signal. In some variations, the startup circuit 430 can include a state machine 435 that may be implemented in hardware to function separate from the controller circuit 420 and to read data from the non-volatile memory circuit and write the data to the one or more of the configuration registers 460.

Figure 5:
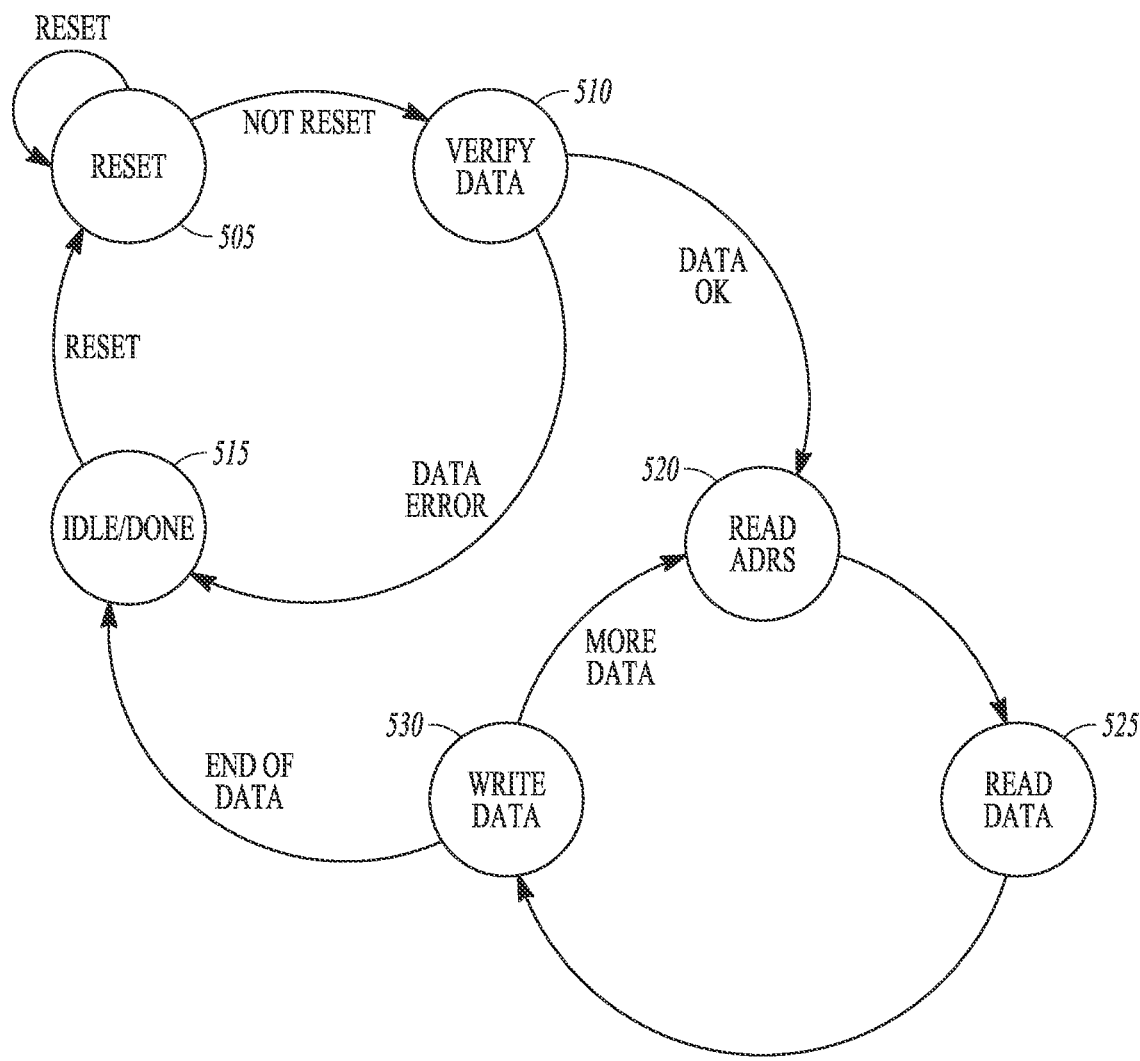
FIG. 5 shows a state diagram of an example of operation of reset and startup of an IMD.

FIG. 5 shows a state diagram of an example of operation of reset and startup of an IMD. The device enters state 505 when reset is asserted. The device may remain in state 505 until reset is no longer asserted, in which case the device advances to transfer auto-configuration data from the memory circuit 405. At state 510, the device may verify the integrity of the auto-configuration data. In some examples, the IMD 410 of FIG. 4 includes an error detection circuit 440 that detects an error in the auto-configuration data. In some variations, the error detection circuit 440 computes a checksum for the data to detect any error in the auto-configuration data. In some variations, the error detection circuit 440 checks parity of the data to detect any error in the auto-configuration data. In some variations, the error detection circuit 440 checks Cyclic Redundancy Check (CRC) of the data to detect any error in the auto-configuration data.

If an error in the data is detected, the device may bypass the states related to the transfer of auto-configuration and enter an idle mode at state 515. In some examples, the controller circuit 420 enters an idle state in response to the detected error in the auto-configuration data. In some examples, the controller circuit 420 is maintained in a reset state in response to the detected error.

If no error is detected at state 505, the device enters a data transfer loop that includes states 520, 525 and 530. The address of an auto-configuration data word is read at state 520. This may include reading a value of the address out of memory or reading a value indicated by a pointer. The data corresponding to the address is read at state 525 and the auto-configuration data word is written to one or more configuration registers at state 530. The device may enter an idle state when the data transfer is completed. The device may remain idle until an event causes the device to leave the auto-configuration mode or until another reset signal is received. The controller circuit 420 may be disabled during the transfer of configuration data such as by maintaining the controller circuit 420 in a reset state. The controller circuit 420 may be released when state 515 is entered.

The values written into the configuration registers configure the IMD 410 for a safety mode operation. The safety mode provides reduced functionality of the IMD 410 in a basic or nominal mode of operation. The safety mode may be entered after reset is inactivated. If the controller circuit 420 includes a processor, a reduced area of firmware may be used by the processor while the device is in the safety mode, or the safety mode can involve the use of no firmware by the processor and the processor can be disabled during the safety mode. A separate device (e.g., a state machine, or separate processor) can be used to implement safety mode. However, because IMDs are typically battery powered, adding components such as a separate processor and memory may adversely impact battery life. Also, adding components may require a printed circuit board (PCB). Additional interconnect for the PCB and components may negatively impact reliability of a device.

Different types of IMDs perform different functions and provide different features. Thus, a different set of auto-configuration data can be stored in the configuration portion of memory for different types of devices. The IMD 410 may include a therapy circuit 445 and writing values in one or more of the configuration registers 460 configures a therapy provided using the IMD 410. For instance, writing a value into a configuration register can configure the IMD 410 as a device to treat slow arrhythmias or bradycardia. Writing a different value into the register (or writing a value into a different register) can configure the IMD 410 as a device to treat fast arrhythmias or tachyarrhythmia. Thus, the same platform can be used for either a low energy device or a high energy device and the auto-configuration data can be changed to tailor the safety mode features to the intended end product.

In some variations, writing a value into a configuration register can configure a safety-mode therapy provided by the IMD 410 when in safety mode operation. For instance, writing a value into a configuration register can configure a multi-chamber IMD as a single chamber device. In this way, circuits dedicated to the unused chambers can be powered down in the safety mode. In some examples, writing a value into a configuration register can enable a shock into short feature. In this feature, a high energy shock device delivers the high energy therapy into a load internal to the device rather than to the subject. This may be desired if the device enters safety mode in response to a detection of a failure or short in a device lead. In some examples, writing a value into a configuration register can configure the IMD 410 as a device to provide electrical therapy to a portion of the nervous system (e.g. stimulation of a portion of the parasympathetic nervous system or a portion of the sympathetic nervous system).

Figure 6:
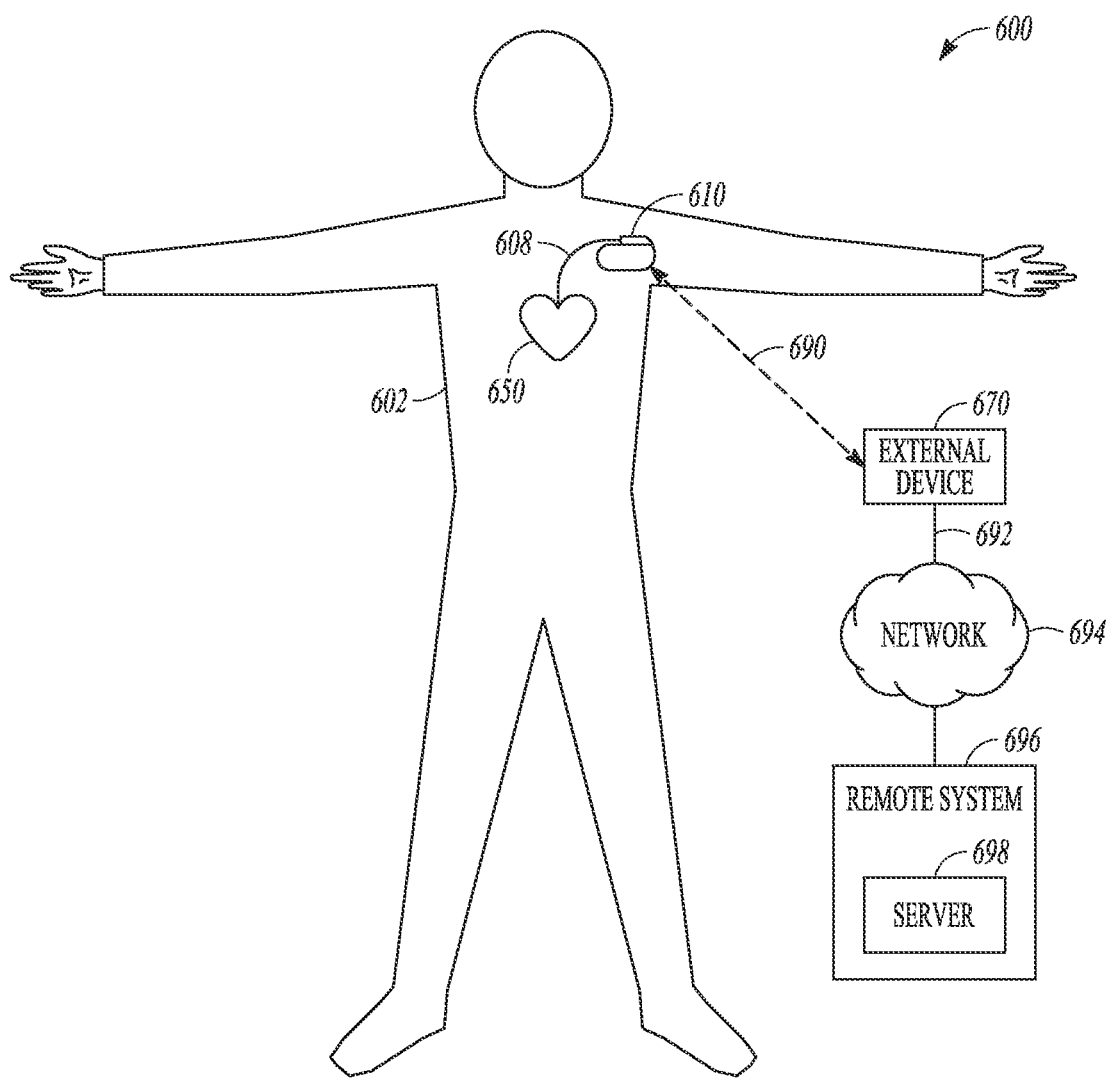
FIG. 6 is an illustration of portions of a system that uses an IMD to provide a therapy to a patient.

The IMD 410 can include a communication circuit 450. According to some examples, writing values in one or more of the configuration registers 460 configures wireless telemetry communication of the IMD 410. FIG. 6 is an illustration of portions of a system 600 that uses an IMD 610 to provide a therapy to a patient 602. The system 600 typically includes an external device 670 that communicates with a remote system 696 via a network 694. The network 694 can be a communication network such as a phone network or a computer network (e.g., the internet). In some examples, the external device 670 includes a repeater and communicates via the network using a link 692 that may be wired or wireless. In some examples, the remote system 696 provides patient management functions and may include one or more servers 698 to perform the functions.

Returning to FIG. 4, writing a value into a configuration register can configure mutual inductance telemetry or near field telemetry of the device, such as by specifying a frequency for the near field telemetry. In some variations, writing a value into a configuration register can enable radio frequency (RF) or far field telemetry of the IMD 410.

The IMD 410 can include one or more sensor circuits 455, and writing values in one or more of the configuration registers configures one or more sensor circuits of the IMD 410. For instance, writing a value into a configuration register may enable an input for a sensor (e.g. an activity sensor). In some variations, writing values in one or more of the configuration registers 460 configures an interface for a type of sensor. For instance, writing a value into a configuration register may configure a filter circuit connectable to a sensor circuit. In some variations, writing a value into a configuration register may configure filtering for an accelerometer signal. This may be useful to accommodate different types of accelerometers or to configure a specific use for an accelerometer.

According to some examples, the IMD 410 can include an integrated circuit (IC). The IC can include one or more of the non-volatile memory circuit, the controller circuit, and the reset circuit. In certain variations, the IC is an application specific integrated circuit (ASIC). The IC can include one or more general purpose input/output (GPIO) pads 465. Writing a value in one or more of the configuration registers 460 configures one or more of the GPIO pads. In some variations, a GPIO can be configured into one of four possible configurations: a) as an input pad without a pull-up or pull-down circuit electrically connected to the input pad, b) as an input pad with a pull-up or pull-down circuit electrically connected to the I/O pad, c) as an output pad that is driven to a logic low value (e.g. electrical ground), or d) as an output pad driven to a high logic value (e.g. the positive supply rail).

As explained previously herein, the reset signal may be generated in response to a detected error. In some examples, the memory may be a memory error. The IMD 410 may include an error detection circuit 440 electrically coupled to the non-volatile memory circuit 405 and adapted to detect a memory error in the memory circuit, wherein the reset circuit is configured to generate the reset signal in response to a detected memory error.

In some examples, the IMD 410 includes a watchdog timer circuit 470. The watchdog timer circuit 470 can include a counter that is recurrently restarted by the controller circuit 420 to prevent the watchdog timer circuit 470 from generating a timeout error signal when reaching a specified count. The timeout error signal can be generated when an error occurs in the controller circuit 420 and the controller circuit 420 fails to reset the watchdog timer. The reset circuit 425 may generate the reset signal in response to the timeout error signal.

In examples where the controller circuit 420 includes a processor circuit adapted to perform instructions, the watchdog timer circuit 470 detects an error condition resulting from the processor circuit making an invalid branch in the instructions. In some variations, the startup circuit 430 transfers auto-configuration data from the configuration memory portion to a portion of the IMD memory (e.g., volatile memory 480) adapted to store processor-performable instructions. The error detection circuit 440 may detect any errors in the instructions performable by the processor circuit. The reset circuit 425 generates the reset signal in response to detection of an error in the instruction. In some variations, the processor circuit is maintained in a disabled state upon completion of the transferring of the auto-configuration data when an error is detected in the instructions. In examples where the controller circuit 420 includes an FSM, the reset circuit is adapted to generate the reset signal in response to an FSM error. The watchdog timer circuit 470 may be useful to detect an FSM error, such as when the FSM enters an invalid state or becomes stuck in one of the machine states.

According to some examples, the reset signal is generated in response to a "brown out" condition of the energy source (e.g., battery). The reset circuit 425 generates the reset signal when a supply voltage exceeds a specified threshold voltage. The controller circuit 420 can be in an idle state upon completion of the transferring of the auto-configuration data in response to the brown out. A brown out can occur towards the end of the life of battery of the IMD 410, or when a rechargeable battery becomes low prior to a recharge. Without the auto-configuration, the IMD 410 could lose the device configuration as a result of the brown out.

The auto-configuration allows flexibility in the final configuration of the device. The final configuration can be determined at the time of manufacturing when the auto-configuration data is written to non-volatile memory such as flash memory. This simplifies the design of an IMD by not having to try and determine what the configuration will be prior to design of the IC (or ICs) of the IMD.

The auto-configuration may also provide a patch mechanism for the IMD. For instance, data values that are to be loaded into volatile memory (e.g. random access memory) can be included in the auto configuration data and written into volatile memory at the time of auto-configuration. In some variations, the flash memory can be configured in the field after manufacturing. The device may be partially implantable and include an external connection to provide the voltage necessary to program the flash memory. In some variations, the device includes a circuit that can generate the voltage necessary for programming the flash memory. This may be useful in a device with a rechargeable power source.

Auto-configuration can be used for configuring the normal operating mode of the IMD in addition to (or alternatively) configuring a safety mode. For instance, configuring the GPIO pads can be useful for a normal operating mode as well as the safety mode. In some variations, writing configuration data into a configuration registers or into a portion of memory can be used to trim a circuit value such as a capacitance value (C) or a resistance value (R). A circuit trim can be useful to set a specific value for C or R to accommodate process variations in the C or R values.

The several examples described herein provide for flexibility in determining a default configuration for an IMD. The auto-configuration provides an alternative to designers having to decide what the configuration will be several years in advance of actual use of the product.

ADDITIONAL NOTES

The above detailed description includes references to the accompanying drawings, which form a part of the detailed description. The drawings show, by way of illustration, specific embodiments in which the disclosure can be practiced. These embodiments are also referred to herein as "examples." In the event of inconsistent usages between this document and any documents incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable medical device (IMD) comprising:
   a non-volatile memory circuit including a configuration memory on to store auto-configuration data for the IMD;
   a controller circuit;
   a reset circuit adapted to generate a reset signal and disable the controller circuit; and
   a startup circuit adapted to transfer the auto-configuration data from the configuration memory portion to one or more configuration registers in response to the reset signal, wherein values of the one or more configuration registers configure the IMD for a safety mode operation.

2. The IMD of claim 1, wherein the startup circuit includes a hardware state machine adapted to function separate from the controller circuit and to read data from the non-volatile memory circuit and write the data to the one or more configuration registers.

3. The IMD of claim 1, including an integrated circuit (IC) that includes one or more of the non-volatile memory circuit, the controller circuit, and the reset circuit, wherein the IC includes one or more general purpose input/output (GPIO) pads, and wherein at least one of the configuration registers configures one or more of the GPIO pads.

4. The IMD of claim 1, wherein at least one of the configuration registers configures wireless telemetry communication of the IMD.

5. The IMD of claim 1, wherein at least one of the one or more configuration registers configures a therapy provided using the IMD.

6. The IMD of claim 1, wherein at least one of the one or more configuration registers configures a safety-mode therapy provided when the IMD is in the safety mode operation.

7. The IMD of claim 1, wherein the controller circuit includes a processor circuit adapted to perform instructions.

8. The IMD of claim 7, wherein the startup circuit is adapted to transfer auto-configuration data from the configuration memory portion to a portion of the IMD memory adapted to store processor-performable instructions.

9. The IMD of claim 7, including an error detection circuit adapted to detect an error in an instruction performable by the processor circuit, wherein the reset circuit is adapted to generate the reset signal in response to detection of the error in the instruction and maintain the processor circuit in a disabled state upon completion of the transferring of the auto-configuration data.

10. The IMD of claim 1, wherein the reset circuit is adapted to generate the reset signal when a supply voltage exceeds a specified threshold voltage, and wherein the controller circuit is in an idle state upon completion of the transferring of the auto-configuration data.

11. The IMD of claim 1, including an error detection circuit adapted to detect an error in the auto-configuration data, wherein the reset circuit is adapted to maintain the controller circuit in at least one of a reset state or an idle state in response to a detected error in the auto-configuration data.

12. The IMD of claim 1, wherein the controller circuit includes a finite state machine (FSM), and wherein the reset circuit is adapted to generate the reset signal in response to an FSM error.

13. The IMD of claim 1, including a watchdog timer circuit configured to generate a timeout error signal when the watchdog timer circuit reaches a specified count without being reset, wherein the reset circuit is configured to generate the reset signal in response to the timeout error signal.

14. The IMD of claim 1, including an error detection circuit electrically coupled to the non-volatile memory circuit and adapted to detect a memory error in the memory circuit, wherein the reset circuit is configured to generate the reset signal in response to a detected memory error.

15. A method of operating an implantable medical device (IMD), the method comprising:
    generating a reset signal in the IMD;
    disabling normal control flow of the IMD in response to the generated reset signal; and
    transferring auto-configuration data from a configuration portion of non-volatile memory of the IMD to one or more configuration registers when normal control flow of the IMD is disabled, wherein values of the one or more configuration registers configure the IMD for a safety mode operation.

16. The method of claim 15, wherein disabling normal control flow includes disabling processor-performable instructions in response to the generated reset signal.

17. The method of claim 16, wherein generating a reset signal includes generating a reset signal when an error is detected in a processor-performable instruction, and wherein processor-performable instructions remain disabled upon completion of the transferring of the auto-configuration data.

18. The method of claim 16, wherein generating a reset signal includes generating a reset signal when a supply voltage exceeds a specified threshold voltage, and wherein processor-performable instructions are enabled upon completion of the transferring of the auto-configuration data.

19. The method of claim 16, wherein transferring auto-configuration data includes transferring auto-configuration data from the configuration portion to a portion of the IMD memory adapted to store processor-performable instructions.

20. The method of claim 15, wherein transferring auto-configuration data from a configuration portion of memory of the IMD to one or more configuration registers includes writing configuration data into one or more configuration registers to configure a safety-mode therapy provided when the IMD is in the safety mode operation.

* * * * *